(12) United States Patent
Chow

(10) Patent No.: US 6,448,574 B1
(45) Date of Patent: Sep. 10, 2002

(54) METHOD AND APPARATUS FOR DETERMINING LIQUID LEVELS IN A LIQUID SAMPLE CONTAINER

(75) Inventor: Allan Tit-Shing Chow, Wilmington, DE (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 09/524,681

(22) Filed: Mar. 14, 2000

(51) Int. Cl.⁷ .............................................. G01F 23/00
(52) U.S. Cl. ......................................... 250/577; 73/293
(58) Field of Search ................................ 250/573, 574, 250/576, 577, 564, 565, 231.1, 900; 356/436, 440, 442; 73/293; 340/619

(56) References Cited

U.S. PATENT DOCUMENTS

| | | |
|---|---|---|
| 3,511,572 A | 5/1970 | Peube et al. |
| 3,569,716 A * | 3/1971 | Lewis .......................... 250/205 |
| 3,636,360 A | 1/1972 | Oishi et al. ................... 250/218 |
| 3,817,625 A * | 6/1974 | Jordan .......................... 250/577 |
| 3,908,441 A | 9/1975 | Virloget .......................... 73/55 |
| 4,448,752 A | 5/1984 | Fujimori et al. ................ 422/81 |
| 4,501,146 A * | 2/1985 | Greenhalgh ................ 73/290 B |
| 4,733,095 A | 3/1988 | Kurahaski et al. ........... 250/577 |
| 4,873,863 A | 10/1989 | Bruhl et al. |
| 5,073,720 A | 12/1991 | Brown ......................... 250/577 |
| 5,274,245 A | 12/1993 | Lee .............................. 250/577 |
| 5,565,977 A | 10/1996 | Rosinko ........................ 356/39 |
| 5,648,844 A | 7/1997 | Clark .......................... 356/5.09 |
| 5,747,824 A | 5/1998 | Jung et al. ................... 250/577 |
| 5,777,221 A | 7/1998 | Murphy et al. ................ 73/149 |

FOREIGN PATENT DOCUMENTS

| | | |
|---|---|---|
| EP | 0185285 | 6/1986 |
| GB | 2293986 | 4/1996 |
| JP | 57208417 | 12/1982 |
| JP | 60200128 | 10/1985 |
| WO | WO 9415181 | 7/1994 |

* cited by examiner

*Primary Examiner*—Kevin Pyo
(74) *Attorney, Agent, or Firm*—Leland K. Jordan

(57) ABSTRACT

Monitoring the intensity pattern of a radiation beam reflected from a sample tube before and after the tube is tilted from an original alignment to determine signal areas that correspond to the location of a liquid interface within the tube.

12 Claims, 8 Drawing Sheets

METHOD AND APPARATUS FOR DETERMINING LIQUID LEVELS IN A LIQUID SAMPLE CONTAINER

FIELD OF THE INVENTION

The present invention generally relates to the determination of the amount of liquid in a sample container. More particularly, the present invention provides a method for determining the interface levels of liquid components in a transparent sample container.

BACKGROUND OF THE INVENTION

Many biological samples such as urine, blood serum, plasma, cerebrospinal fluid and the like, are stored in a closed sample container after collection or pretreatment. Popularly used sample containers are transparent glass or plastic tubes to facilitate visual or machine inspection of various characteristics of the enclosed sample liquid, including color, volume, uniformity, etc. When samples are to be used for biochemical analysts, it is desirable to know if the amount of available sample fluid contained in the tube is sufficient to provide adequate volume to perform a single or a number of analytical tests. It is most desirable to determine the total sample fluid volume available for testing prior to opening a closed sample container and prior to beginning a sample division or aliquot process to ensure that ample sample is available or to prioritize the tests to be completed if an insufficient amount of sample is available.

Known methods to determine the volume of assorted liquids within closed sample tubes include the use of a photo-electrical detector in conjunction with a radiation beam. Typically, the beam is passed through the tube and captured by the detector, the detected signal being processed to ascertain the level of liquid, usually by analyzing the signal in order to determine some special feature within the signal. The volume of sample available for testing may be determined, depending on the diameter of the tube.

U.S. Pat. No. 5,747,824 discloses an array of four infrared LED's and an array of four phototransistor receivers with each LED and phototransistor mounted inside a radiation baffle. The LEDs are positioned in a substantially vertical array just outside one side wall of the cassette. The vertical line on which the LEDs are arranged is substantially parallel to the direction in which the fluid/air interface moves within the cassette. The LEDs are aimed upwardly at an angle of approximately 20 degree(s) from horizontal. A corresponding substantially vertical array of four phototransistor receivers is mounted outside the cassette opposite the LEDs such that each of the receivers is aimed at its corresponding LED.

U.S. Pat. No. 5,274,245 discloses a device for detecting a specific liquid level, which can be mounted externally on a transparent or translucent vessel wall, and is insensitive to ambient radiation. This device utilizes a single radiation detector and a pair of AC activated radiation sources. The radiation sources produce reflected radiation signals which, when balanced at the detector, cancel. When liquid is absent the radiation signals are balanced, and no signal is detected. When liquid is present the extra signal reflected by the meniscus causes the radiation signals to become unbalanced, and a signal is detected.

U.S. Pat. No. 5,073,720 discloses a liquid level measurement device is an electro-optical device which uses a radiation source (typically a radiation emitting diode or laser diode) and an optical detector to measure the level of a liquid in a container. The radiation beam is passed through the liquid and received by the optical detector. The detector output is processed to determine the liquid level or the liquid volume.

U.S. Pat. No. 4,733,095 discloses a method for detecting a liquid level is monitored at mutually opposing sides of a liquid containing bottle. For monitoring the liquid level at each side of the bottle, a diffused radiation beam is irradiated toward the liquid surface from a level below the liquid surface. The radiation reflected at the liquid surface and the radiation refracted at the liquid surface are detected by a photo-receiving camera which is focused at a standard liquid level. An average value of the monitored liquid levels at both sides is taken as a liquid level indicative value.

U.S. Pat. No. 3,908,441 discloses a device for detecting the level of a liquid in a transparent tube including a radiation source to be placed facing a region of the periphery of the tube and a photocell to be placed facing a second zone of the tube periphery to receive radiation totally reflected from the internal face of the tube which has been wetted by a liquid, and which contains air rather than liquid. The device may be embodied in an automatic viscometer especially for colored or opaque liquids.

U.S. Pat. No. 3,636,360 discloses a method for photo-electronically detecting a liquid level by projecting a radiation beam to a transparent tube communicating with a pressure liquid tank and detecting the redirected radiation beam, utilizing the difference of relative refractivity at the inner wall of the tube when liquid fills the tube and when not, and the apparatus. Means for receiving the radiation beam redirected from the tube is so disposed as to receive the radiation beam only when the tube is empty, or the liquid is lower than the detector.

Accordingly, from a study of the different approaches taken in the prior art to the problems encountered with detecting the level of a liquid in a tube, there is a need for a simplified method, especially a method employing readily available detecting means.

SUMMARY OF THE INVENTION

Many of disadvantages of using complex analysis schemes and/or sophisticated equipment within the prior art are overcome by using the apparatus and/or methods of this invention. This invention provides a method for determining the level of a liquid in a sample tube by monitoring the intensity pattern of an radiation beam that has been transmitted through or reflected from the sample tube before and after the tube is tilted from an original alignment relative to the interrogating radiation beam. The captured radiation beam intensity pattern changes in those signal areas that correspond to the location of a liquid interface within the tube. By observing the position of such changes, it is possible to easily determine the levels of liquids having different refractive indices within the tube. Such a simplified approach makes it possible to accurately determine, for example, the upper level of a liquid within a closed sample tube without resorting to image analysis or other such techniques.

Associated with this method is an apparatus for automatically determining the liquid level within a sample tube using readily available electro-optical equipment in conjunction with a device for rotating a sample tube to expose a transparent portion of the sample tube surface to an interrogating optical beam and then tilting the tube to cause the level of liquid within the tube to vary its vertical position.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
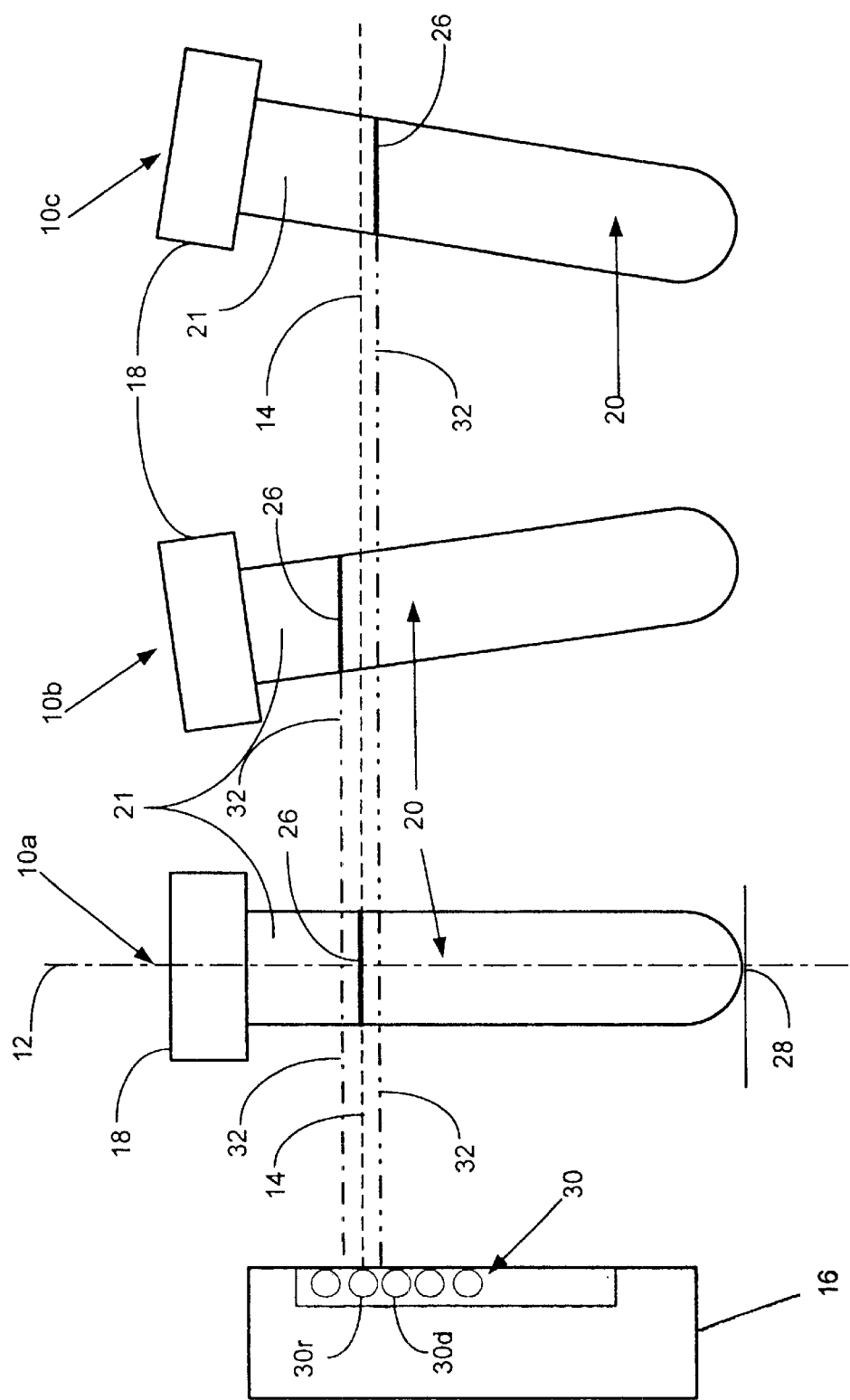
FIG. 1 is a schematic elevation view of an electro-optic analyzer with which the present invention may be practiced.

FIG. 1 shows schematically the important elements needed to practice the present invention. It is known that the amount of radiation incident upon, for example, a semi-transparent glass liquid sample tube, will be reflected by an amount that depends upon the relative values of the optical indices of refraction of any liquid segment or gas segment occupying the tube. Generally, the index of refraction of the liquid segment will be greater than the index of refraction of the gas portion so that a greater amount of incident radiation will be reflected from the tube. By monitoring the amplitude of such reflected radiation, the location of the interface between the liquid and gas segments may be determined. However, a number of external and generally uncontrolled variables affect the amount of reflected radiation so that it is not adequately reliable to rely only upon determining a single amplitude change in the intensity of reflected radiation. The present invention overcomes this limitation by comparing the amplitude of radiation reflected from the tube when the tube is positioned at two different angles relative to the incident radiation.

Tube 10a illustrates an instance in which the vertical axis 12 of tube 10 in the 10a position is perpendicularly oriented relative to the direction traversed by an interrogating beam of radiation 14 shown with dashed lines and produced within an electro-optical detector 16 described hereinafter. Tube 10b illustrates an instance in which the vertical axis 12 of the tube 10 is inclined about 10 degrees relative to the direction traversed by the interrogating beam of radiation 14 and in a direction where the top of tube 10b is moved more closely towards the electro-optical detector 16. Tube 10c illustrates an instance in which the vertical axis 12 of the tube 10 is inclined about 10 degrees relative to the direction traversed by the interrogating beam of radiation 14 and in a direction where the top of the tube 10c is moved away from the electro-optical detector 16. Thus, the beam of radiation 14 is perpendicularly incident upon tube 10a and tubes 10b and 10c are titled in a direction parallel to the beam of radiation. The embodiment of tube 10a having a vertical position is not required to practice the present invention; it is only important that there be at least two different alignments between tubes 10a and 10b relative to the incident radiation beam.

Tube 10 is shown closed with a cap 18 although the present invention does not require the tube 10 to be closed and may be practiced in either sample tube embodiment. Tube 10 contains at least one liquid segment 20 that partially fills tube 10 and a gas segment 21 that fills the reminder of tube 10. Liquid segment 20 has a upper surface 26 and in a first embodiment, one object of the invention is to locate the position of or location of upper surface 26 relative to the bottom 28 of tube 10.

A vertical array 30 of electro-optical cells, comprising for example a plurality of individual radiation-light-emitting diodes 30d (LED's) and a plurality of individual photoelectric receptors 30r, is contained in electro-optical detector 16 and the plurality of individual LED's 30d are disposed in a manner to provide a semi-continuous vertically oriented band of interrogating radiation beam 14 comprising individual radiation rays produced by the LED's 30d. For purposes of clarity, only a few LED's 30d and only one interrogating radiation beam 14 are shown. The band of interrogating radiation 14 is directed toward tubes 10a, 10b or 10c in a manner such that individual photoelectric receptors 30r also contained in electro-optical detector 16 capture radiation rays 32 shown in a dash-dot line which are reflected from tubes 10a, 10b or 10c backwards towards detector 16. For purposes of clarity, only one interrogating radiation ray 14 and two reflected radiation rays 32 are shown and one individual photoelectric receptors 30r, however both rays are to be understood as illustrative of a semi-continuous vertically oriented bands of radiation and the individual photoelectric receptor 30r as illustrative of a plurality of such individual photoelectric receptors 30r.

Obviously in an equivalent arrangement, interrogating radiation 14 from the diodes could be transmitted through tubes 10a, 10b or 10c and captured as traversing radiation after traversing tubes 10a, 10b or 10c by an array of receptors positioned on the opposite side of tubes 10a, 10b or 10c from the detector 16. Exemplary electro-optical cells 30 comprising individual radiation-light-emitting diodes 30d and photoelectric receptors 30r useful in performing this invention are well-known in the art and may be like the solid stage imaging device described in U.S. Pat. No. 4,148,048 assigned to Hitachi wherein a two-dimensional solid-state imaging device is disclosed containing a plurality of picture elements each consisting of a photodiode and a switching insulated-gate field effect transistor disposed on the same semiconductor substrate. Since the photodiodes are discrete devices, they may be arranged in a vertical manner to provide the a semi-continuous vertically oriented band of interrogating radiation 14, the beam being semi-continuous because of discontinuities between next adjacent photodiodes.

For the purpose of a simplified illustration, a single interrogating radiation ray 14 is shown in FIG. 1 as being incident upon tube 10a near the location of the upper surface 26 of liquid segment 20. Because tube 10a has its vertical axis 12 perpendicular to the interrogating radiation ray 14, the reflected radiation beam 32 generated by interrogating beam 14 will be reflected towards the vertical array of electro-optical cells 30 along the same path as taken by beam 14 and will be captured by a photoelectric receptor 30r at the height position corresponding to the upper surface 26 of liquid segment 20. It is convenient to pre-determine the locations of individual photoelectric receptors 30r within the vertical array of electro-optical cells 30 relative to the bottom, or top, of tube 10 to facilitate a subsequent calibration. This may be done, for example, by physically positioning the bottom of tube 10 in alignment with the lowermost individual photoelectric receptor 30r within the array 30. In an alternate equivalent arrangement, the bottom of tube 10 may be positioned a known distance below the lowermost individual photoelectric receptor 30r within the array 30. In either instance, intensity pattern of the reflected radiation beam 32 from the upper surface 26 of the liquid segment 20 as captured by the individual photoelectric receptor 30r corresponding to the reflected radiation beam 32 provides a first indication of the location of the upper surface 26 of liquid segment 20 relative to the bottom 28 of tube 10a.

Figure 2:
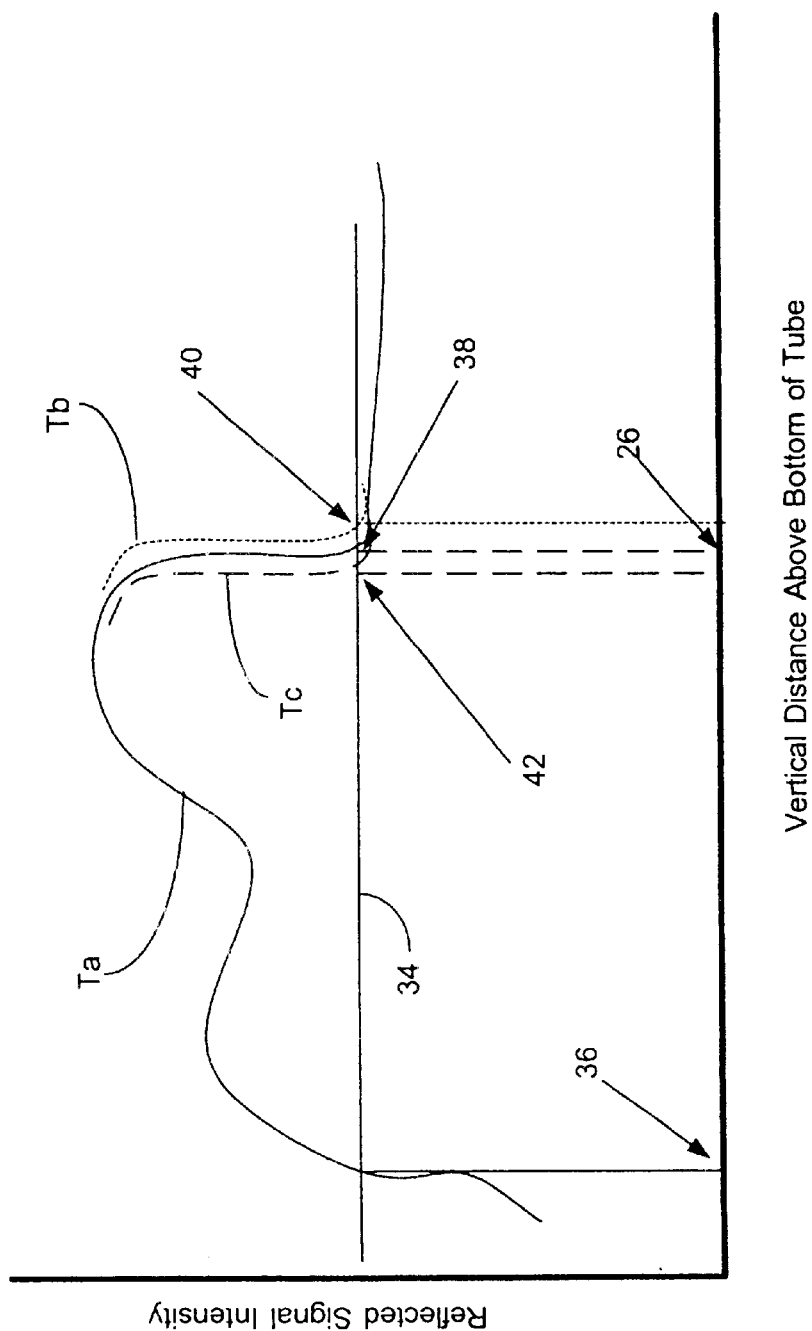
FIG. 2 is an exemplary plot of captured signals using the electro-optic analyzer of FIG. 1 to analyze a tube containing a single liquid segment.

It is known that the amount of interrogating radiation 14 captured as reflected radiation 32 by array 30 depends upon the relative values of the optical indices of refraction of the liquid segment 20 and of the gas segment 21 occupying the uppermost, unfilled portion of tube 10a. Generally, the index of refraction of the liquid segment 20 will be greater than the index of refraction of the gas segment 21 and a greater amount of reflected radiation 32 will be reflected back towards array 30. In the instance that the interrogating radiation beam 14 is perpendicularly incident upon tube 10a (the vertical axis 12 of the tube 10 is perpendicular to the direction of the interrogating beam 14), the magnitude of the beam 32 reflected back to the detector 16 is illustrated by solid line Ta and this signal generally increases as portions of the radiation beam 14 are reflected back to the detector 16 and converted therein to detected signal values. At that vertical height position 20 on tube 10 corresponding to the top level of the liquid segment 20 within tube 10, the reflected signal Ta drops to and even falls below the baseline zero signal 34. To practice the present invention, the first intensity pattern of the reflected radiation beam 32 from the upper surface 26 of the liquid segment 20 within tube 10a may be plotted as a function of position or height of the upper surface 26 within tube 10a because of the aforementioned calibration of the position of the individual photoelectric receptors 30r relative to the bottom 28 of vertically oriented tube 10a. An exemplary first intensity pattern of the radiation beam 32 reflected from the upper surface 26 of the liquid segment 20 within tube 10a is shown in FIG. 2 as a solid line trace Ta.

The amount of reflected radiation 32 captured within the individual photoelectric receptors 30r is affected by a number of external variables such as ambient radiation levels, optical indices of refraction of the tube material, typically glass, amplitude of interrogating radiation, cleanliness of the tube, etc. Consequently, it is not totally reliable to rely only upon determining a single amplitude change in the intensity of reflected radiation 32 captured within photoelectric receptors 30r. A key feature of the present invention is the elimination of ambiguities introduced by such variables by obtaining a second reflected radiation signal pattern indicative of the location of the upper surface 26 of liquid segment 20 relative to the bottom 28 of tube 10 when tube 10a is tilted a few degrees relative to vertical, with the top of the tube 10b being closer to the array 30 than the top of tube 10a, as illustrated by tube 10b in FIG. 1. In the instance that the interrogating radiation beam 14 is incident upon tube 10a at an angle less than 90-degrees (that is, the vertical axis 12 of the tube 10 is inclined towards the detector 16), for example about 10 degrees, the magnitude of the beam 32 reflected back to the detector 16 is illustrated by dot-dashed line Tb. At that vertical height position 20 on tube 10b corresponding to the higher top level of the liquid 20 within tube 10b (as the tube is inclined towards the detector, the top of the liquid 20 rises within tube 10b), the reflected signal 32 drops to and falls below the baseline zero signal 34 at a height value higher than 26, as indicated by 40 on the horizontal axis of the plot. Again, using the same technique as described above, a second intensity pattern of the reflected radiation beam 32 from the upper surface 26 of the liquid segment 20 within tube 10b may be plotted as a function of position or height of the upper surface 26 within tube 10b because of the aforementioned calibration of the position of the individual photoelectric receptors 30r relative to the bottom 28 of vertically oriented tube 10a. An exemplary second intensity pattern of the radiation beam 32 reflected from the upper surface 26 of the liquid segment 20 within tube 10b is shown in FIG. 2 as a dotted line trace Tb. During this process, the bottoms of tubes 10a, 10b and 10c are maintained at the same height.

Figure 3:
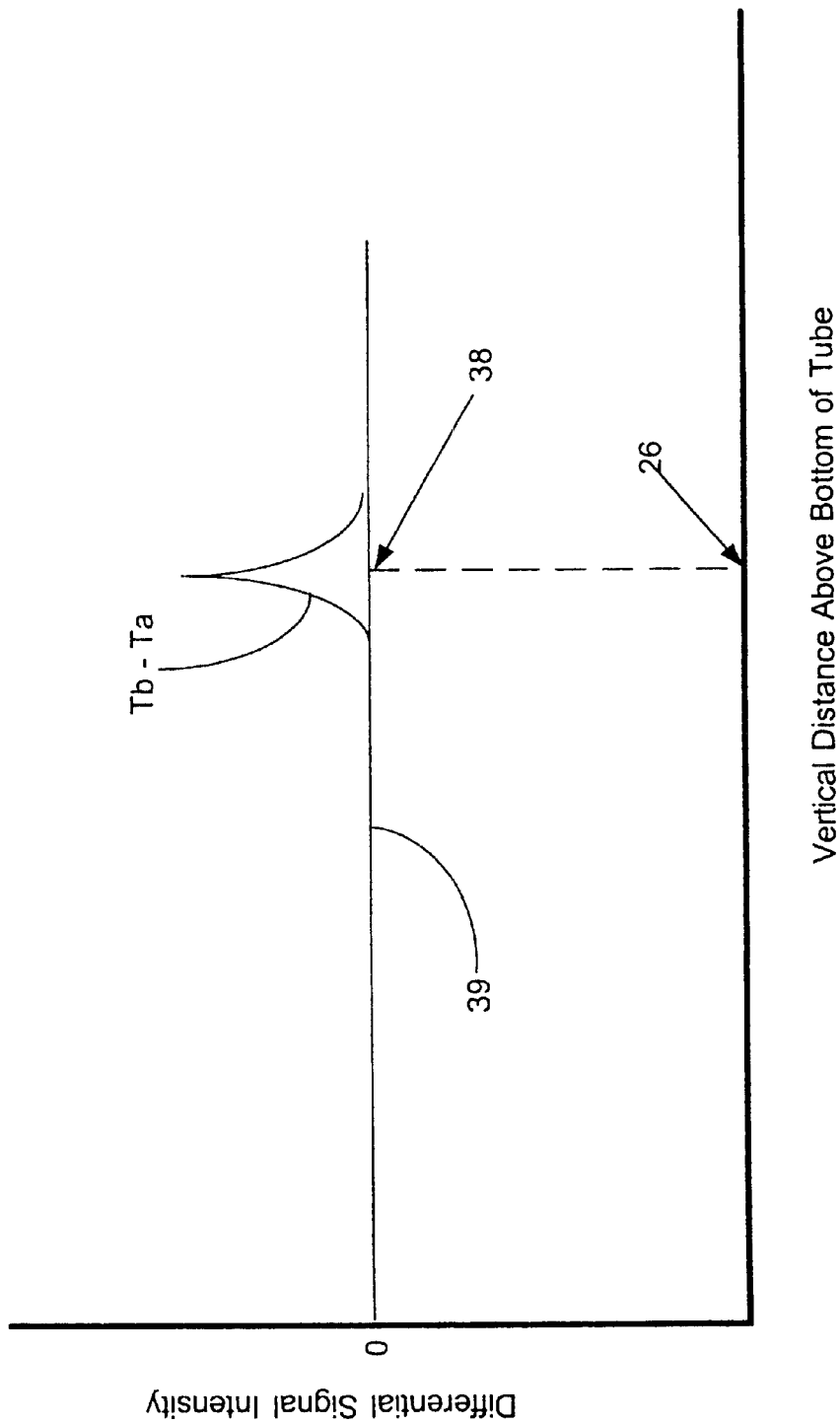
FIG. 3 is an exemplary plot of differential signal intensities using the electro-optic analyzer of FIG. 1 for a tube containing a single liquid segment.

By comparing the first and second traces Ta and Tb of reflected radiation 32 captured within the individual photoelectric receptors 30r and corresponding to the position or height along tube 10a, it is possible to accurately determine the location of a gas-liquid interface 26 relative to the bottom or top of tube 10a. When tube 10a is titled to the orientation of tube 10b in accord with the teachings of this invention, at the location corresponding to the interface, the corresponding first and second traces Ta and Tb of reflected radiation are most widely disparate. This is illustrated in FIG. 2 where the reflected signal intensity of signal traces Ta and Tb is shown as a function of the height or vertical along tube 10. Note that the reflected signal intensity from the portion of liquid 20 within tubes 10a and 10b not displaced by tilting tube 10a to position 10b remains unchanged so that the leftmost portion of trace Tb is the same as the leftmost portion of trace Ta. The onset of reflected radiation begins at a vertical location 36 corresponding to the bottom of tube 10a or 10b at a relative reflected signal intensity 34. Signal intensity traces Ta and Tb positively increase above this initial value 34 until falling back close to value 34 at two different points 38 and 40, corresponding to radiation being reflected from tubes 10a and 10b at two different positions indicative of the location of the liquid surface 26 in tubes 10a and 10b, respectively. Because tube 10b is tilted so that the top of tube 10b is closer to the electro-optical detector 30, the inclined liquid level 26 occurs at a greater distance from the bottom of tube gob so that trace Tb intersects the signal value 34 line at a greater vertical distance above the bottom of tube 10b. The relative vertical distances above the bottom of tube 10 corresponding to the points at which Ta and Tb intersect the signal value 34 serve to accurately define the location of the upper surface 26 without errors arising from such interfering effects as mentioned above. It is convenient but not necessary in practicing the present invention to subtract the two traces Ta and Tb yielding a difference curve Tb–Ta like that shown in FIG. 3 to facilitate a rapid location of the upper surface 26 as corresponding to the peak value at point 38 along a zero-difference line 39.

An equivalent effect may be achieved by tilting tube 10a a few degrees relative to vertical, with the top of the tube 10 being further from the array 30 than the top of tube 10a, as illustrated by tube 10c in FIG. 1. An exemplary third intensity pattern of the radiation beam 32 reflected from the upper surface 26 of the liquid segment 20 within tube 10c is shown in FIG. 2 as a dashed line trace Tc. Again, the onset of reflected radiation begins at a value 34 corresponding to the bottom of tube 10a or 10c. Signal intensity traces Ta and Tc positively increase above this initial value 34 until falling back close to value 36 at two different points 38 and 42, corresponding to radiation being reflected from tubes 10a and 10c at a position indicative of the location of the liquid surface 26 in tubes boa and 10c, respectively. In this instance, tube 10c is tilted so that the top of tube 10c is further from the electro-optical detector 30 than is tube boa, so that the inclined liquid level 26 occurs at a lesser distance from the bottom of tube 10c. Consequently, trace Tc intersects the signal value 34 line at a lesser vertical distance above the bottom of tube 10c. The relative vertical distances above the bottom of tube 10 corresponding to the points at which Ta and Tc intersect the signal value 34 serve to accurately define the location of the upper surface 26 without errors arising from interfering effects. Again, it is convenient but not necessary in practicing the present invention to subtract the two traces Ta and Tc yielding a difference curve to facilitate a rapid location of the upper surface 26.

Figure 4:
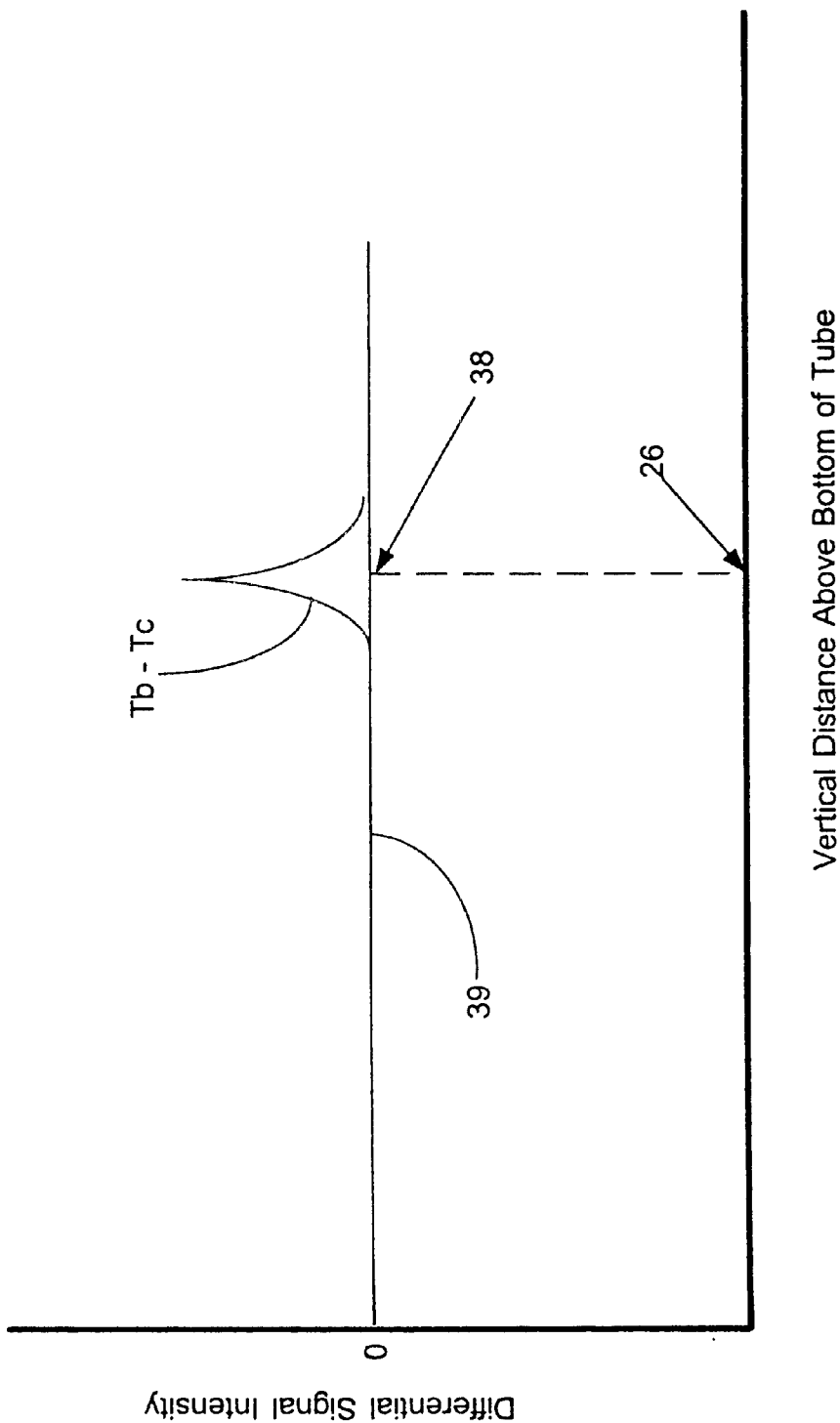
FIG. 4 is an alternate exemplary plot of captured signals using the electro-optic analyzer of FIG. 1 for a tube containing a single liquid segment.

Reference herein to a single photoelectric receptor 30r is for purposes of clarity and should not be interpreting as limiting in definition or scope. It is understood that due to spreading of the reflected beam 32, more than one photoelectric receptor 30r will capture the reflected beam 32; as illustrated in FIG. 2, the output signals from array 30 of electro-optical cells are correspondingly spread over a small range. Furthermore, as previously mentioned, it is only important that there be at least two different alignments between tubes 10a and 10b relative to the incident radiation beam to achieve the accuracy provided by the present invention in locating the position of liquid level 26. This may be illustrated by comparing traces Tb and Tc, which are respectively representative of tube 10b and tube 10c which have two different alignments therebetween relative to the incident radiation beam, and neither having a perpendicular alignments relative to the incident radiation beam. In this instance, it is not necessary to subtract the two traces Tb and Tc to provide a difference curve Tb–Tc like that shown in FIG. 4 to locate the upper surface 26, however such an embodiment of the present invention is convenient.

Figure 5:
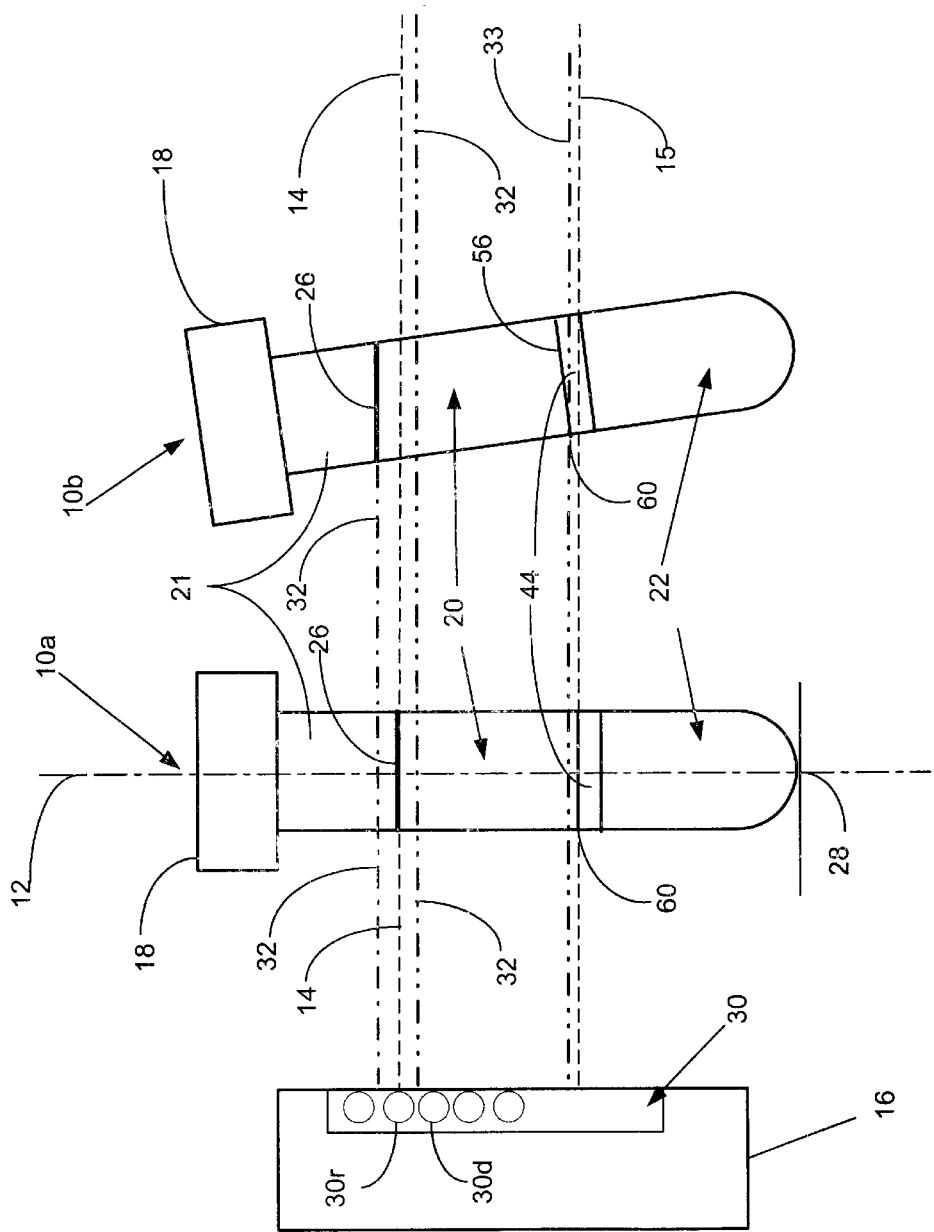
FIG. 5 is a schematic elevation view of an electro-optic analyzer in which an alternate embodiment of the present invention may be practiced to analyze a tube containing two liquid segments separated by a gel-like layer.

A second liquid 22 is shown in FIG. 5 to illustrate a further alternate embodiment of the present invention in which an additional liquid segment 22 is also contained in tube 10, the two liquid segments 20 and 22 being separated by a gel-like layer 44, liquid segment 22 in the lowermost portion of tube 10. Again, for the purpose of a simplified illustration, a single interrogating radiation ray 14 is shown in FIG. 5 as being incident upon tube 10a near the location of the upper surface 26 of liquid segment 20 and another single interrogating radiation ray 15 is shown as a dashed line in FIG. 5 as incident upon tube 10a near the location 56 of the surface of the gel-like layer 44 separating the two liquid segments 20 and 22. Because tube 10a has its vertical axis 12 perpendicular to the interrogating radiation ray 14, the reflected radiation beam 32 generated by interrogating beams 14 and 15 will be reflected towards the vertical array of electro-optical cells 30 along the same paths as taken by beams 14 and 15 and will be captured by a photoelectric receptor 30r at the height positions corresponding to the upper surface 26 of liquid segment 20 and to the location 56 of the surface of the gel-like layer 44.

Figure 6:
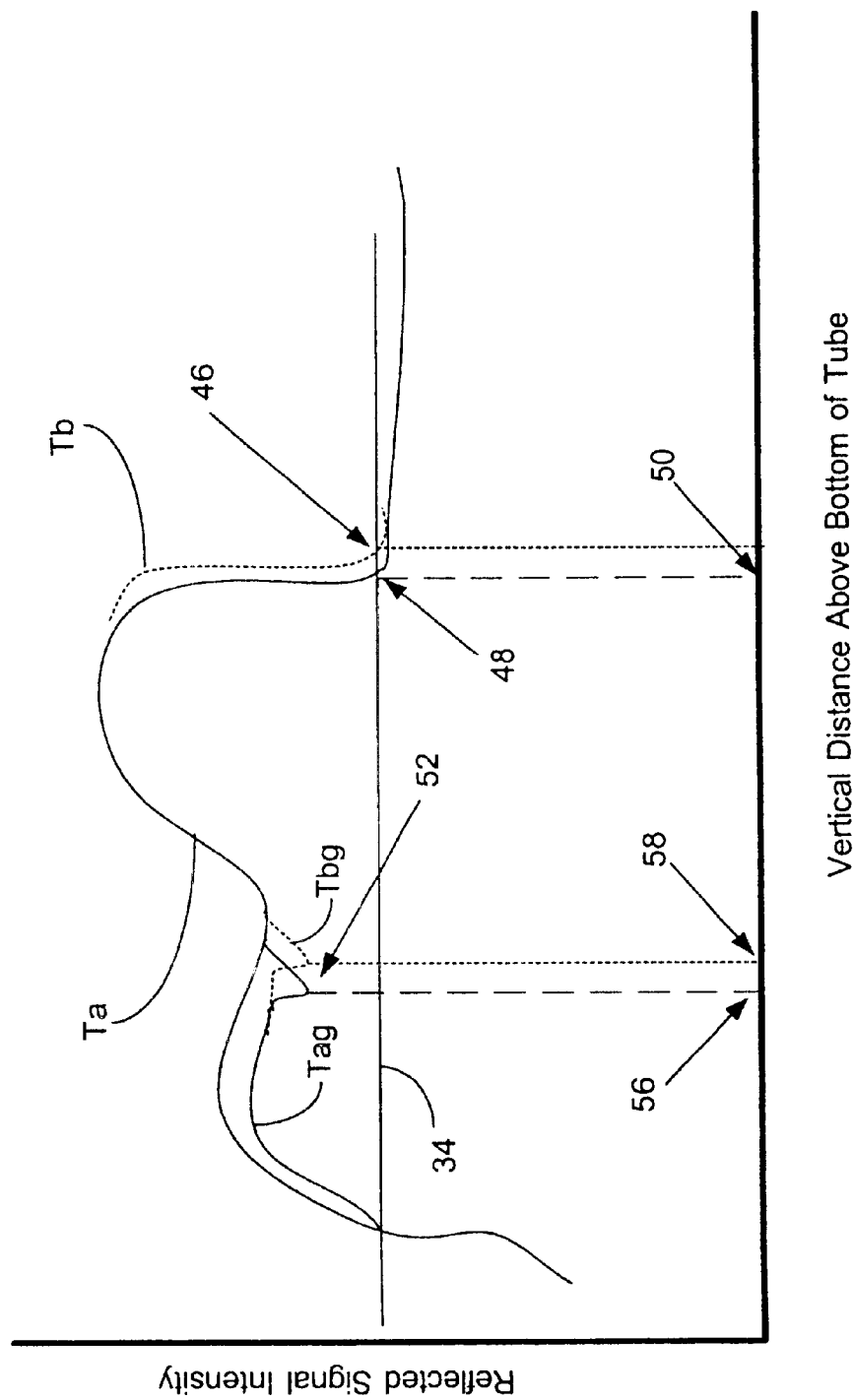
FIG. 6 is an exemplary plot of captured signals using the electro-optic analyzer of FIG. 5 to analyze a tube containing two liquid segments separated by a gel-like layer.

The amount of interrogating radiation 14 and 15 captured as reflected radiation 32 and 33, respectively, by array 30 depends upon the relative values of the optical indices of refraction of the liquid segments 20 and 22 and of the gel-like layer 44 within tube 10a. In the instance that the interrogating radiation beams 14 and 15 are perpendicularly incident upon tube, the magnitude of the corresponding beams 32 and 33 reflected back to the detector 16 is illustrated in FIG. 6 by solid lines Ta and Tag, respectively, and these signals generally increase as portions of the radiation beams 14 and 15 are reflected back to the detector 16 and converted therein to detected signal values. At that vertical height position on tube 10 corresponding to the top level 26 of the liquid 20 within tube 10, the reflected signal Ta drops to and even falls below the baseline zero signal 34 as generally indicated by 48. However, at that vertical height position on tube 10 corresponding to the location 60 of the surface of the gel-like layer 44 within tube 10a, the reflected signal Tag decreases as generally indicated by 52 but does not drop below the baseline zero signal 34 and then rejoins trace Ta when signals are again reflected from that portion of tube 10b containing liquid segment 20.

In FIG. 5, tube 10b illustrates the vertical axis 12 of the tube 10 as inclined about 10 degrees relative to tube 10a in a direction where the top of tube 10b is moved more closely towards the electro-optical detector 16. In this instance, the magnitude of the beams 32 and 33 reflected back to the detector 16 is illustrated in FIG. 6 by dotted lines Tb and Tbg, respectively. At that vertical height location on tube 10b corresponding to the higher level of the liquid 20 within tube 10b, the reflected signal 32 drops below the baseline zero signal 34, as indicated by 46 on the horizontal axis of the plot in FIG. 6. At that vertical height location on tube 10b corresponding to the higher level of the gel-like layer 44 within tube 10b, the reflected signal 33 intersects trace Ta at a higher corresponding location on tube 10b, as indicated by 58 on the horizontal axis of the plot in FIG. 6.

Figure 7:
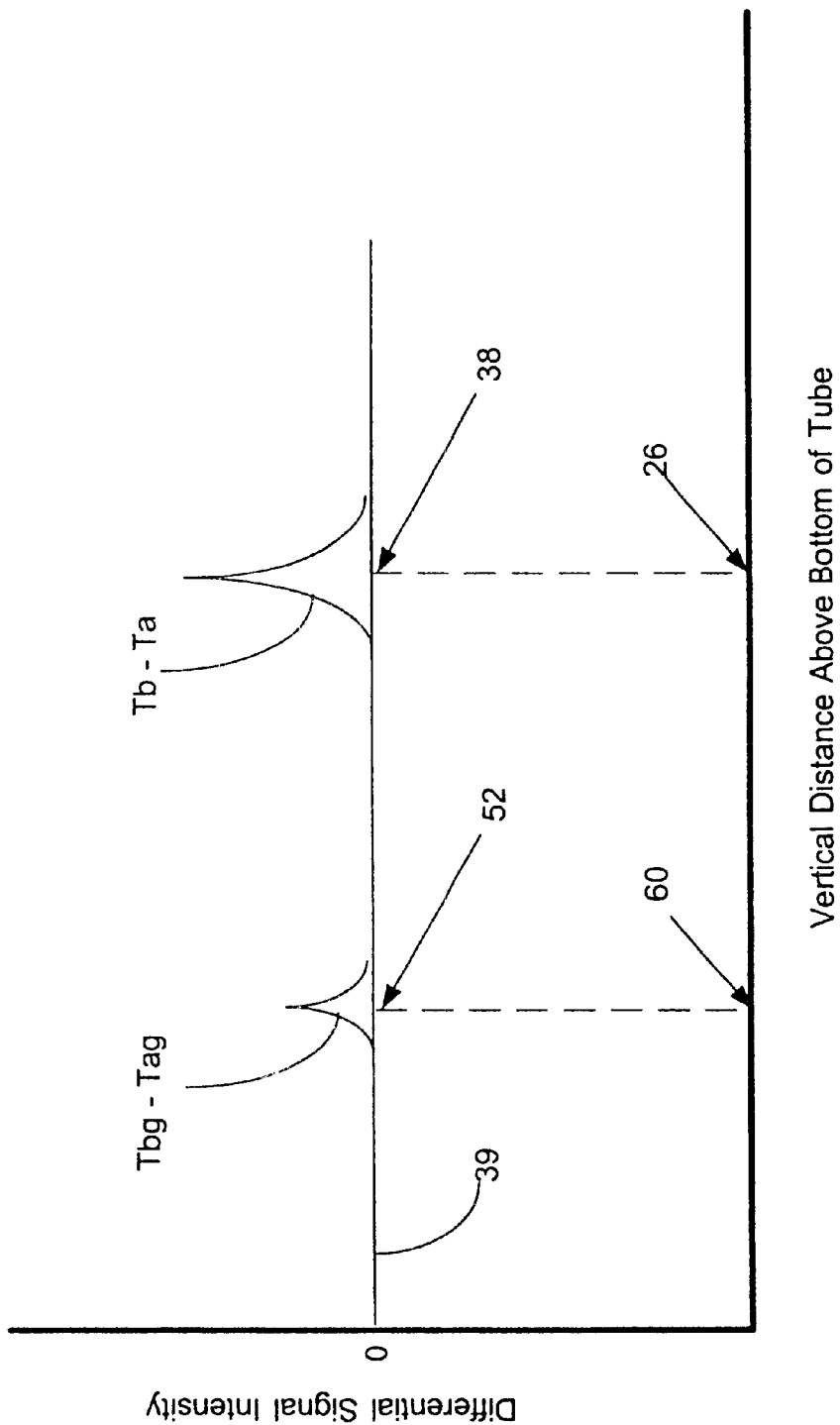
FIG. 7 is an exemplary plot of differential signals using the electro-optic analyzer of FIG. 1 to analyze a tube containing two liquid segments separated by a gel-like layer; and, FIG. 8 is a schematic plan view of an electro-optic analyzer in which an alternate embodiment of the present invention may be practiced to determine the level of a liquid in a tube.

In this embodiment, comparing the first and second traces Tag and Tbg of reflected radiation 32 captured within the individual photoelectric receptors 30r, enables an accurate determination of the location of the gel-like layer 44 relative to the bottom or top of tube 10a. When tube 10a is titled to the orientation of tube 10b in accord with the teachings of this invention, at the location corresponding to the interface, the corresponding traces Tag and Tbg of reflected radiation are most widely disparate. Signal intensity traces Tag and Tbg positively increase above initial value 34 until rejoining trace Ta at two different points generally indicated at 52, corresponding to radiation being reflected from tubes 10a and 10b at two different positions indicative of location of the gel-like layer 44. Because tube 10b is tilted so that the top of tube 10b is closer to the electro-optical detector 30, the gel-like layer 44 is located at a greater distance from the bottom of tube 10b so that trace Tbg intersects the signal value trace Ta at a greater vertical distance above the bottom of tube 10b. The relative vertical distances above the bottom of tube 10 corresponding to the points at which Tag and Tbg intersect trace Ta, 56 and 58 respectively, serve to accurately define the location 60 of the gel-like layer 44 in tube 10 without errors arising from such interfering effects as mentioned above. It is convenient but not necessary in practicing the present invention to subtract the two traces Ta and Tb and the two traces Tag and Tbg yielding a differential curve like that shown in FIG. 7 to facilitate a rapid location of the location 60 of the gel-like layer 44 as well as a rapid location of the upper surface 26 of the uppermost liquid segment in tube 10a. In this instance, there are two regions of greatest difference in the differential curve corresponding to the location 60 of the gel-like layer 44 as well to the location of the upper surface 26 of the uppermost liquid segment 20.

Figure 8:
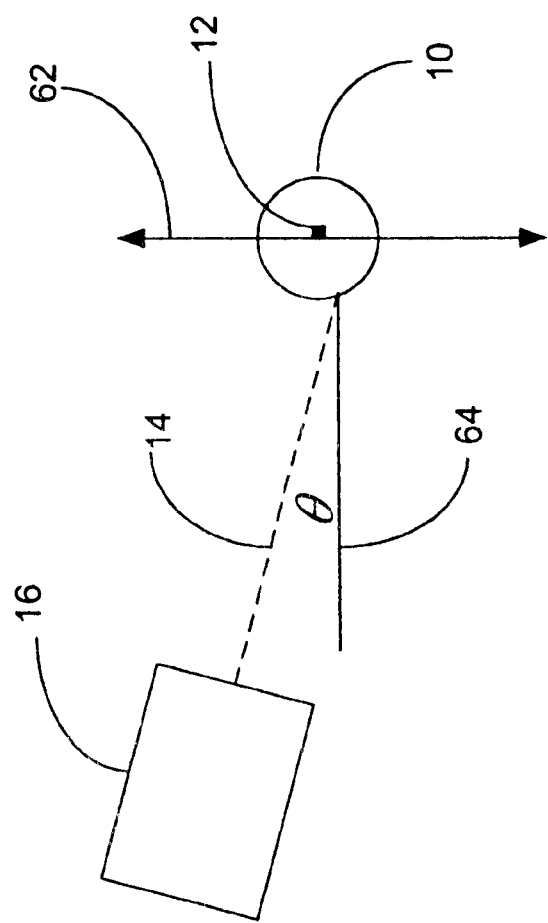

FIG. 8, taken with FIGS. 1–4, illustrates another alternate embodiment of the present invention whereby a change in the position of the upper surface of a liquid within a tube 10 is indicative of the level of liquid in the tube when the vertical orientation of the tube is altered. In this instance, the detector 16 is purposefully disposed so that the interrogating radiation beam 14 makes an angle Ø with a line 64 perpendicular to a plane of inclination 62 located along the centerline 12 of the tube. Angle Ø is in the range of about 5 to 10 degrees in magnitude and the detector 16 is also located so that the radiation beam 14 strikes tube 10 near a vertical edge of tube 10 as illustrated. In an arrangement like the one of FIG. 8, tube 10 may be titled in either direction within plane 62 as indicated by the two arrows on plane 62 and the change in position of the upper surface of a liquid within tube 10 measured in a manner similar to that described hereinabove. Although beam 14 is shown striking tube 10 near a vertical edge so that the magnitude of the changed position of the upper surface of the liquid within tube 10 is maximized, this is an expedient condition and is not required to make the level position measurement. The only requirement is that detector 16 be designed and positioned so that a change in liquid level position is detectable by detector 16, in combination with radiation beam 14, regardless of the direction tube 10 is inclined from an original position.

It is to be understood that the embodiments of the invention disclosed herein are illustrative of the principles of the invention and that other modifications may be employed which are still within the scope of the invention. For example, for tubes without a gel-like layer 44, once the location of the upper surface 26 of liquid segment 20 is determined, it is possible to calculate from the diameter of tube 10 the volume of liquid 20 available for analysis. And, for tubes with a gel-like layer 44, once the locations of the upper surface 26 of liquid segment 20 and of the gel-like layer 44 are determined, it is possible to calculate from the diameter of tube 10 the volumes of liquids 20 and 22 available for analysis. Similarly, the exact means used for tilting the tube between different orientations is not critical in practicing the present invention; a cup-like holder may be placed over the bottom or top of the tube and mechanically translated by a lever or transducer to provide the desired amount of tilt. Alternately, a clasp may be used to grip the tube circumferentially and then the clasp rotated to provide the desired amount of tilt. These means have not been illustrated due to their simplistic engineering nature but are included here for completeness. Accordingly, the present invention is not limited to those embodiments precisely shown and described in the specification but only by the following claims.

What is claimed is:

1. A method for determining the level of a liquid in a sample tube by:

measuring the intensity of a first beam of radiation transmitted through or reflected from the upper surface of liquid within the sample tube in a first orientation;

tilting the tube to a second orientation;

measuring the intensity of a second beam of radiation transmitted through or reflected from the upper surface of liquid within the sample tube in said second orientation; and, correlating changes between the first and second intensities to determine the level of the liquid within the tube.

2. The method of claim 1 wherein an electro-optical detector is used to provide or measure the beam of radiation transmitted through or reflected from the tube.

3. The method of claim 1 wherein the beam of radiation is perpendicularly incident upon the tube and the tube is titled in a direction along the beam of radiation.

4. The method of claim 1 wherein the difference between the first and second tube orientations is about 10 degrees.

5. The method of claim 1 wherein correlating changes between the first and second intensity patterns comprises determining the difference between the first and second intensity patterns and selecting the region of greatest difference.

6. The method of claim 2 wherein the detector is disposed so that the interrogating radiation beam strikes the tube at an angle relative to a line perpendicular to a plane of inclination located along the centerline of the tube.

7. The method of claim 6 wherein the tube is titled within the plane of inclination.

8. A method for determining the level of a gel-like layer separating two liquids in a sample tube by:

measuring the intensity of a first beam of radiation transmitted through or reflected from the gel-like layer in the sample tube in a first orientation;

tilting the tube to a second orientation;

measuring the intensity of a second beam of radiation transmitted through or reflected from the gel-like layer in the sample tube in the second orientation;

measuring a second intensity pattern of the beam of radiation transmitted through or reflected from the gel-like layer in the sample tube in said second orientation; and, determining the level of the gel-like layer within the tube by comparing the first and second beam intensities and selecting the region of greatest difference to identify the level of the gel-like layer within the tube.

9. The method of claim 8 wherein an electro-optical detector is used to provide or measure the beam of radiation transmitted through or reflected from the tube.

10. The method of claim 8 wherein the beam of radiation is perpendicularly incident upon the tube and the tube is titled in a direction along the beam of radiation.

11. The method of claim 8 wherein the difference between the first and second tube orientations is about 10 degrees.

12. An apparatus useful for determining the level of a liquid in a sample tube, the apparatus comprising:

an electro-optical detector for measuring the intensity pattern of a beam of radiation transmitted through or reflected from the upper surface of liquid within the sample tube;

means for tilting the tube from a first orientation to a second orientation; and, means for correlating changes between the intensity pattern in the first orientation and in the second orientation to the upper surface level of the liquid within the tube.

* * * * *